US011613518B2

(12) United States Patent
Faessler et al.

(10) Patent No.: US 11,613,518 B2
(45) Date of Patent: Mar. 28, 2023

(54) PLANT AND METHOD FOR PURIFYING AN ISOMERIC MONOMER

(71) Applicant: Sulzer Management AG, Winterthur (CH)

(72) Inventors: Peter Faessler, Allschwil (CH); Manfred Stepanski, Buchs (CH); Halbe Jansen, Eschlikon (CH)

(73) Assignee: SULZER MANAGEMENT AG, Winterthur (CH)

( * ) Notice: Subject to any disclaimer, the term of this patent is extended or adjusted under 35 U.S.C. 154(b) by 332 days.

(21) Appl. No.: 16/771,367

(22) PCT Filed: Nov. 26, 2018

(86) PCT No.: PCT/EP2018/082529
§ 371 (c)(1),
(2) Date: Jun. 10, 2020

(87) PCT Pub. No.: WO2019/115213
PCT Pub. Date: Jun. 20, 2019

(65) Prior Publication Data
US 2021/0179547 A1 Jun. 17, 2021

(30) Foreign Application Priority Data
Dec. 14, 2017 (EP) .................................. 17207511

(51) Int. Cl.
*C07C 265/14* (2006.01)
*B01D 3/26* (2006.01)
(Continued)

(52) U.S. Cl.
CPC .............. *C07C 265/14* (2013.01); *B01D 1/22* (2013.01); *B01D 3/26* (2013.01); *B01D 5/0003* (2013.01);
(Continued)

(58) Field of Classification Search
CPC ........... C07C 7/04; C07C 7/14; C07C 263/20; C07C 265/14; B01D 3/26; B01D 3/42; B01D 3/4205; B01D 5/006; B01D 5/009
See application file for complete search history.

(56) References Cited

U.S. PATENT DOCUMENTS 4,118,410 A 10/1978 Friedel et al.
4,189,354 A 2/1980 Ellendt et al.
(Continued)

FOREIGN PATENT DOCUMENTS

CN 1550493 A 12/2004
CN 101003497 A 7/2007
(Continued)

OTHER PUBLICATIONS

English machine translation of CN 101003498, copyright Clarivate Analytics. (Year: 2007).*
(Continued)

*Primary Examiner* — Renee Robinson
(74) *Attorney, Agent, or Firm* — Global IP Counselors, LLP

(57) ABSTRACT

A plant for preparing a purified isomeric methylene diphenyl diisocyanate monomer from a mixture of different isomeric monomers is disclosed herein. The plant can comprise a distillation apparatus, which comprises: a) a distillation column including a structured packing, b) a source for a mixture of different isomeric methylene diphenyl diisocyanate monomers, c) an evaporator, d) an overhead vapor condenser, e) optionally, an overhead vacuum system and f) a flow-controlled reflux system. The overhead vapor condenser comprises a shell and tube arrangement and is embodied so as to directly subcool the condensate to less than 47° C. The flow-controlled reflux system comprises a heater, which is embodied so as to reheat a partial stream of
(Continued)

the condensate formed in the overhead vapor condenser up to 190° C.

13 Claims, 3 Drawing Sheets

(51) Int. Cl.
  *B01D 5/00* (2006.01)
  *B01D 1/22* (2006.01)
  *B01D 9/00* (2006.01)
  *C07C 263/20* (2006.01)

(52) U.S. Cl.
  CPC ............. *B01D 5/006* (2013.01); *B01D 5/009* (2013.01); *B01D 9/0013* (2013.01); *C07C 263/20* (2013.01); *B01D 2009/0086* (2013.01)

(56) References Cited

U.S. PATENT DOCUMENTS

| | | | |
|---|---|---|---|
| 4,360,476 A * | 11/1982 | Green | C07C 263/20 560/352 |
| 4,414,074 A | 11/1983 | Ellendt et al. | |
| 7,649,108 B2 | 1/2010 | Schal et al. | |
| 9,505,711 B2 | 11/2016 | Bock et al. | |
| 2008/0275269 A1 | 11/2008 | Keggenhoff et al. | |
| 2012/0123153 A1 | 5/2012 | Bock et al. | |

FOREIGN PATENT DOCUMENTS

| | | |
|---|---|---|
| CN | 101003498 A | 7/2007 |
| EP | 1734035 A1 | 12/2006 |
| GB | 1417087 | 12/1975 |
| GB | 1570741 | 7/1980 |
| JP | S539750 A | 1/1978 |
| JP | S5890540 A | 5/1983 |
| JP | 2014500876 A | 1/2014 |

OTHER PUBLICATIONS

Hearing Notice issued in corresponding Indian Application No. 202017023447 on May 2, 2022.
Chinese Office Action dated Jan. 11, 2022 in corresponding Chinese Application No. 201880080586.3.
Chinese Search Report dated Dec. 23, 2021 in corresponding Chinese Application No. 201880080586.3.
International Search Report dated Jan. 25, 2019 in corresponding International Patent Application No. PCT/EP2018/082529, filed Nov. 26, 2018.
International Preliminary Report on Patentability and Written Opinion dated Jun. 16, 2020 in corresponding International Patent Application No. PCT/EP2018/082529, filed Nov. 26, 2018.
Zhu Zhengde et al., "Production Technology and Development of Diphenylmethane Diisocyanate"; Liaoning Chemical Industry, vol. 35, No. 11, c. 2006.
Japanese Office Action dated Aug. 12, 2022 in corresponding Japanese Patent Application No. 2020-529740.

* cited by examiner

PLANT AND METHOD FOR PURIFYING AN ISOMERIC MONOMER

CROSS-REFERENCE TO RELATED APPLICATION

This application is a U.S. National Stage application of International Application No. PCT/EP2018/082529, filed Nov. 26, 2018, which claims priority to European Patent Application No. 17207511.1, filed Dec. 14, 2017, the contents of each of which are hereby incorporated herein by reference.

BACKGROUND

Field of the Invention

The present disclosure relates to a plant for preparing a purified isomeric monomer from a mixture of different isomeric monomers, and in particular to a plant for preparing purified 4,4'-methylene diphenyl diisocyanate from a crude mixture of methylene diphenyl diisocyanate including among others different isomers of methylene diphenyl diisocyanate, namely 4,4'-methylene diphenyl diisocyanate and at least one of 2,2'-methylene diphenyl diisocyanate and 2,4'-methylene diphenyl diisocyanate, as well as dimers of methylene diphenyl diisocyanate, oligomers of methylene diphenyl diisocyanate, polymers of methylene diphenyl diisocyanate and lights, such as dichlorobenzene. Moreover, the present disclosure relates to a process for preparing a purified isomeric monomer from a crude mixture including different isomeric monomers as well as dimers, oligomers and polymers thereof, and in particular to a process for purifying 4,4'-methylene diphenyl diisocyanate from a crude methylene diphenyl diisocyanate mixture including different isomers, dimers, oligomers and polymers of methylene diphenyl diisocyanate, which contains 4,4'-methylene diphenyl diisocyanate and at least one of 2,2'-methylene diphenyl diisocyanate and 2,4'-methylene diphenyl diisocyanate, wherein the process is performed in the aforementioned plant.

Background Information

Methylene diphenyl diisocyanate, which is abbreviated as MDI, exists in the form of three isomers, namely in the form of 2,2'-methylene diphenyl diisocyanate, in the form of 2,4'-methylene diphenyl diisocyanate, as well as in the form of 4,4'-methylene diphenyl diisocyanate. 4,4'-Methylene diphenyl diisocyanate is by far the most widely used from these three isomers. In particular, 4,4'-methylene diphenyl diisocyanate is an important compound for producing rigid polyurethanes. More specifically, rigid polyurethanes are prepared from 4,4'-methylene diphenyl diisocyanate in admixture with one or more polyols and optionally a blowing agent. Rigid polyurethanes are in turn desirable due to their excellent thermal insulation properties important materials, which are used for instance in freezers, refrigerators and buildings.

SUMMARY

At present, methylene diphenyl diisocyanate is produced by phosgenating methylene diphenyl diamines. More specifically, methylene diphenyl diisocyanate is often produced with a method comprising the following steps: i) forming methylene diphenyl diamines and polyamines of the diphenylmethane series by reacting aniline and formaldehyde in the presence of an acid catalyst, and b) phosgenating the methylene diphenyl diamines and polyamines of the diphenylmethane series to produce a mixture of the MDI isomers and polymeric MDI. Afterwards, the obtained crude mixture of methylene diphenyl diisocyanate including among others the MDI isomers, MDI dimers, MDI oligomers, MDI polymers and lights, such as dichlorobenzene, (which is subsequently abbreviated as "crude MDI mixture"), is purified so as to obtain the desired purified MDI isomer, such as in particular to obtain purified 4,4'-methylene diphenyl diisocyanate.

A typical method for purifying a crude MDI mixture is a distillation performed with two or more distillation columns. In the first column, which is usually called crude MDI distillation column, the crude MDI mixture is separated into a bottom fraction being rich in polymeric MDI and a head fraction being rich in 2,2'-MDI, 2,4'-MDI and 4,4'-MDI. The head fraction being rich in 2,2'-MDI, 2,4'-MDI and 4,4'-MDI is fed into a second column, which is usually called isomers distillation column, in which the mixture is separated into a bottom fraction being rich in polymeric MDI and MDI dimers, a lower medium fraction being rich in 4,4'-MDI, a higher medium fraction being rich in 2,4'-MDI and 2,2'-MDI and a head fraction being rich in lights, such as dichlorobenzene.

It is also known to perform a melt crystallization with the fraction being rich in 4,4'-MDI obtained in the second isomer distillation column, in order to increase the 4,4-MDI content of say 95% to more than 99% by weight.

U.S. Pat. No. 4,189,354 discloses a process for the production of MDI isomers having an adjusted content of chlorine compounds comprising the steps of: (a) subjecting a MDI mixture to a first distillation stage whereby MDI isomers are obtained as head product, (b) subjecting the head product to a second distillation stage using a recycle ratio of from 0.1 to 10 and wherein from 0.5 to 10% by weight of the feed into said second distillation stage is removed as the sump product, (c) subjecting the head product of the second distillation stage to a third distillation stage whereby readily volatile impurities are freed therefrom, and (d) working up the sump product of said third distillation stage to obtain purified 2,4'- and 4,4'-diisocyanatodiphenyl methane.

However, a major disadvantage of the aforementioned MDI isomer purification methods requiring a plurality of distillation columns is that they are expensive to operate and require a very complex plant. Moreover, the MDI isomer purification methods making use of melt crystallization have the disadvantage that the melt crystallization does not significantly reduce the content of MDI dimers. However, a high MDI dimer content negatively affects the melt crystallization due to several reasons. Firstly, the high MDI dimer content causes the formation of very fine crystals leading to a cloudy liquor during the crystallization. Secondly, the high MDI dimer content affects the further growth velocity and size of the monomeric MDI having an impact to the final product quality. A high MDI dimer content of more than 200 ppm may also affect distillation plants, since such a high MDI dimer content leads to fouling for instance in the condenser, which is therefore difficult to clean.

In view of this, one object underlying the present disclosure is to provide a plant and a method for preparing a purified isomeric monomer from a crude MDI mixture, which leads to a reduced concentration of MDI dimer in the purified product and which can be operated with comparably low operation costs.

In accordance with the present disclosure, this object is satisfied by providing a plant for preparing a purified isomeric methylene diphenyl diisocyanate monomer from a mixture of different isomeric monomers, wherein the plant comprises a distillation apparatus, which comprises:
a) a distillation column including a structured packing,
b) a source for a mixture of different isomeric methylene diphenyl diisocyanate monomers,
c) an evaporator,
d) an overhead vapor condenser,
e) optionally, an overhead vacuum system and
f) a flow-controlled reflux system,
wherein the overhead vapor condenser comprises a shell and tube arrangement and is preferably embodied so as to directly subcool the condensate to less than 47° C., and wherein the flow-controlled reflux system comprises a heater, which is preferably embodied so as to reheat a partial stream of the condensate formed in the overhead vapor condenser up to 190° C.

This solution bases on the finding that by the combination of the aforementioned measures, the dimer concentration in the condensed head product is significantly reduced and in particular reduced to less than 200 ppm. This is in particular achieved by performing the condensation of the overhead vapor so as to directly subcool the condensate to less than 47° C. It has been found that this reduces the dimer formation. Due to the low MDI dimer content, a fouling in the condenser, which is embodied as a shell and tube condenser, is reliably avoided, so that the condenser can be easily cleaned. Moreover, on account of the low dimer content, the condensed head product is the ideal starting material for a further purification in a subsequent dynamic crystallization apparatus, such as a falling-film or suspension crystallization apparatus, preferably a suspension crystallization apparatus, because—due to the low dimer content—the formation of very fine crystals leading to a cloudy liquor during the crystallization and further affecting the growth velocity and size of the monomeric MDI having an impact on the final product quality is reliably avoided.

Since a partial stream of the condensate, which is fed back into the distillation column via the flow-controlled reflux system, is heated to a temperature of up to 190° C., a precipitation of dimer in the reflux liquid is reliably avoided. Such a dimer precipitation in the reflux liquid would lead to a clogging of the distributor openings. Moreover, the heating of the partial stream of the condensate formed in the overhead vapor condenser, which is fed back into the distillation column via the flow-controlled reflux system, to a temperature of up to 190° C. reliably avoids a vapor condensation in the distillation column due to the entry of cold liquid and thus avoids a high energy loss and enables a high reflux rate. A high reflux rate has a positive impact on the distributor openings, because the openings do not have to be very small and therefore the risk of blocking them by precipitates, such as of MDI dimer, is significantly reduced. In addition, the heating of the partial stream of the condensate formed in the overhead vapor condenser, which is fed back into the distillation column via the flow-controlled reflux system, to a temperature of up to 190° C. increases the admissible reflux rate.

All in all, the plant and process in accordance with various embodiments of the present disclosure allow to obtain as the condensed head product of the distillation column, i.e. as condensate or condensed phase, respectively, after the distillation column a purified isomeric methylene diphenyl diisocyanate monomer with a low MDI dimer content, such as purified 4,4'-methylene diphenyl diisocyanate having for instance the following characteristics:
i) a dimer content of less than 200 ppm, preferably of at most 150 ppm, more preferably of at most 100 ppm, still more preferably of at most 70 ppm and most preferably of at most 60 ppm, and/or
ii) a content of polymeric methylene diphenyl diisocyanate of at most 2000 ppm, preferably of at most 1500 ppm, more preferably of at most 1000 ppm and most preferably of at most 800 ppm, and/or
iii) a color of at most 100 APHA, preferably a color of at most 50 APHA, more preferably a color of at most 40 APHA, and/or
iv) a hydrolyzable chloride content of 10 to 150 ppm, preferably of 30 to 90 ppm, more preferably of 50 to 80 ppm and most preferably of 65 to 75 ppm, and/or
v) a content of 4,4'-methylene diphenyl diisocyanate of 88 to 96% by weight, preferably of 90 to 95% by weight and more preferably of 92 to 94% by weight.

While the dimer content is for instance determined by FTIR spectroscopy according to ASTM D8036, the content of 4,4'-methylene diphenyl diisocyanate is for instance determined by HPLC-UV analysis according to ASTM D7252, the hydrolysable chloride content is for instance determined by HCl acidity measurement by argentometric determination according to ASTM D5523, and the APHA color is measured for instance in accordance with the visual ASTM D1209 APHA/Pt—Co Color scale or in accordance with the instrumental ASTM D5386 method.

Preferably, the condensed phase fulfils at least two, more preferably at least three, even more preferably at least four, at most preferably all of the aforementioned criteria i) to v).

Finally, the plant in accordance with the present disclosure requires less operation costs than a classical purification plant comprising two or more distillation columns.

In accordance with one embodiment of the present disclosure, the plant does not comprise any further distillation column than the one described above, i.e. the plant in accordance with one embodiment the present disclosure only comprises one distillation column. In particular, the plant in accordance with one embodiment of the present disclosure preferably does not contain an isomers distillation column.

In accordance with another embodiment of the present disclosure, the plant further comprises downstream of the distillation apparatus a dynamic crystallization apparatus. Preferably, in this embodiment, the dynamic crystallization apparatus is a falling-film crystallization apparatus or a suspension crystallization apparatus. More preferably, the dynamic crystallization apparatus is a suspension crystallization apparatus. The dynamic crystallization apparatus is connected with the distillation apparatus preferably so that a major partial stream of the condensed and subcooled liquid obtained in the overhead vapor condenser, which is withdrawn from the overhead vapor condenser and thus from the distillation apparatus, is subsequently fed as liquid feed into the suspension crystallization apparatus. This allows to further purify the target isomer, such as in particular 4,4'-methylene diphenyl diisocyanate. Apart from leading to a product with a reduced dimer content, this embodiment requires still less operation costs than a classical purification plant comprising two or more distillation columns.

Preferably, in an embodiment, the suspension crystallization apparatus further comprises a wash column apparatus. This allows an efficient separation of the crystals of purified isomeric monomer from the mother liquor.

For instance, the wash column apparatus may comprise:
a cylindrical vessel, wherein the cylindrical vessel comprises:
a piston with a piston head and a piston rod, wherein the piston is arranged reciprocatingly movable in the cylindrical vessel, wherein the piston bounds below the piston head a wash chamber inside the cylindrical vessel and wherein the piston head comprises at least one filter means,
an inlet for supplying a crystal suspension mixture composed of crystals and mother liquor into the cylindrical vessel,
an outlet for discharging mother liquor from the cylindrical vessel,
an outlet for discharging crystals and/or crystal melt from the cylindrical vessel,
a circulation conduit for circulating melt arranged outside the cylindrical vessel, which is in communication with the wash chamber,
a means arranged in the wash chamber for restricting the movement of the crystal bed that has been compacted in the wash chamber by the piston and for directing the wash liquid entering into the cylindrical vessel from the circulation conduit so as to homogeneously distribute it over the entire cross-section of the cylindrical vessel, wherein the means are preferably a rotating scraper or a static grid.

For the sake of clarification, it is noted that the inlet for supplying a crystal suspension mixture composed of crystals and mother liquor into the cylindrical vessel may be a line, which is directly connected to the housing of the cylindrical vessel, or the inlet may be within the piston rod, which opens out at the end of the piston rod ending in the piston head.

As set out above, the plant in accordance with an embodiment of the present disclosure is particularly suitable for purifying 4,4'-MDI from a crude MDI mixture. Thus, the source for the mixture of different isomeric monomers is preferably a source for a mixture of different isomers of methylene diphenyl diisocyanate, which comprise 4,4'-methylene diphenyl diisocyanate and at least one of 2,2'-methylene diphenyl diisocyanate, 2,4'-methylene diphenyl diisocyanate, as well as MDI dimers, MDI oligomers, MDI polymers and lights. Accordingly, it is preferred that the source for the mixture of different isomeric monomers comprises 4,4'-methylene diphenyl diisocyanate and at least one of 2,2'-methylene diphenyl diisocyanate, 2,4'-methylene diphenyl diisocyanate and oligomers thereof. The oligomer comprises preferably 3 or more rings, such as 3 to 5 rings. For example, the source for the mixture of different isomeric monomers may be a reactor, reactor train, system or plant for phosgenating methylene diphenyl diamines.

For instance, the crude MDI mixture may comprise 30 to 70% by weight, preferably 40 to 60% by weight and more preferably 52 to 58% by weight of 4,4' MDI, 0.5 to 10% by weight, preferably 1 to 7% by weight and more preferably 3 to 5% by weight of 2,4' MDI, 0.01 to 1% by weight, preferably 0.05 to 0.2% by weight and more preferably 0.075 to 0.125% by weight of 2,2' MDI, 0.1 to 10% by weight, preferably 0.5 to 2% by weight and more preferably 0.75 to 1.25% by weight of MDI dimers and 10 to 70% by weight, preferably 20 to 60% by weight and more preferably 30 to 50% by weight of MDI oligomers comprising 3 or more rings.

A particularly important feature of an embodiment of the present disclosure is to embody the overhead vapor condenser as shell and tube arrangement so as to directly subcool the condensate to less than 47° C. This is one of the major measurements assuring a low dimer content of less than 200 ppm in the purified isomeric monomer. Preferably, the overhead vapor condenser is embodied as shell and tube arrangement and so as to directly subcool the condensate to less than 46° C., more preferably to at most 45° C., and most preferably to at most 42° C.

In a further development of the idea of an embodiment of the present disclosure, it is suggested that the evaporator is a falling film evaporator or a thin film evaporator and more preferably a falling film evaporator. In this embodiment, the average residence time of the liquid and vapor is comparable low in the evaporator, which reduces or even completely avoids the formation of dimers in the evaporator. Preferably, the evaporator is arranged outside of the distillation column and more preferably between the source for the mixture of different isomeric monomers and the distillation column.

In accordance with another embodiment of the present disclosure, the structured packing has a specific surface area 100 to 750 $m^2/m^3$, preferably of 150 to 350 $m^2/m^3$, more preferably of 200 to 300 $m^2/m^3$, and most preferably of 225 to 275 $m^2/m^3$. This leads to a particular efficient mass and heat transfer between the descending liquid phase and the ascending gas phase and thus to a complete or at least almost complete removal of the dimers from the ascending gas, since the dimer is efficiently washed out by the descending liquid. This contributes to a low dimer content in the head fraction of the distillation column and thus also to a low dimer content of the liquid being condensed in the overhead vapor condenser.

Furthermore, it is preferred in an embodiment that the distillation column only comprises one bed of structured packing and not more than one bed of structured packings. The presence of one bed of structured packing leads to a shorter average residence time of the liquid and particularly of the vapor in the structured packing in comparison to the presence of two or more beds of structured packings. This is due to the fact that in the case of two or more beds, the residence time for vapor and liquid is increased due to the resistance between the transition of two beds.

A reduction of the average residence time in the distillation column contributes to a reduction of the dimer formation in the structured packing and thus to a reduced fouling in the structured packing and to an increased operational safety.

Preferably, in an embodiment, the distillation column comprises above the structured packing an open channel splash distributor. Such an open channel splash distributor allows a homogeneous distribution of the liquid over the cross-section of the structured packing and allows to precisely adjust the volume of liquid distributed onto the structured packing so as to precisely control the reflux ratio.

In an embodiment, the flow-controlled reflux system is preferably arranged downstream of the overhead vapor condenser and particularly between the overhead vapor condenser and the distributor being arranged above the structured packing. More specifically, it is preferred that the flow-controlled reflux system comprises a line which is connected with an outlet line of the overhead vapor condenser, through which the condensed liquid is withdrawn from the overhead vapor condenser. Through this line of the flow-controlled reflux system a partial stream of the condensed liquid, which is withdrawn from the overhead vapor condenser, is diverged and transferred to the distributor, which is arranged above the structured packing. In accordance with an embodiment of the present disclosure, the flow-controlled reflux system further comprises a heater, through which the reflux liquid may be heated—in the case of purifying a MDI mixture—to a temperature of up to 190° C. and preferably to 150 to 180° C. and preferably to about 180° C. Thereby, a fouling in the distributor can be reliably avoided.

Moreover, it is preferred in an embodiment that the plant comprises a cold trap between the overhead vapor condenser and the overhead vacuum system.

In a further development of the idea of an embodiment of the present disclosure, it is suggested that the distillation column further comprises a sump, which has a smaller diameter than the section of the distillation column above the sump. This leads to a reduced residence time of liquid in the sump and thus contributes to a reduced generation of dimers in the distillation column.

Preferably, the different parts of the plant in accordance with various embodiments of the present disclosure are connected with each other as follows: The source for the mixture of different isomeric monomers, such as preferably for crude MDI mixture, is via a line in fluid connection with the evaporator, in which the mixture is evaporated. In turn, the evaporator is via a line in fluid connection with an inlet of the distillation column, wherein the inlet is arranged at the lower end of the distillation column. The head of the distillation column is via a line in fluid connection with the overhead vapor condenser, in which the vapor is condensed. A condensed liquid outlet line arranged at the lower end of the overhead vapor condenser is via one line in fluid connection with the inlet of the flow-controlled reflux system and thus with the heater of the flow-controlled reflux system, wherein the lower end of the overhead vapor condenser is via a different line preferably further in fluid connection with the inlet of the optional suspension crystallization apparatus. In turn, the heater of the flow-controlled reflux system is via a line in fluid connection with the distributor arranged above the structured packing of the distillation column. Moreover, the overhead vapor condenser is provided with a vapor outlet line, which is in fluid connection with the overhead vacuum system, which in turn is via a line in fluid connection with an inlet at the upper part of the distillation column. A further outlet line is provided at the sump of the distillation column, which is via one line in fluid connection with the inlet line into the evaporator and which is furthermore connected with an outlet line for withdrawing a fraction rich in polymeric MDI from the plant. The suspension crystallization apparatus is provided with two outlet lines, one for withdrawing the fraction with purified 4,4' MDI and one for withdrawing the other fraction.

In accordance with a second aspect, an embodiment of the present disclosure relates to a process for preparing a purified isomeric methylene diphenyl diisocyanate monomer from a crude mixture including among others different isomeric monomers as well as dimers, oligomers and polymers thereof, wherein the process is performed in a plant as described above.

Preferably, in an embodiment, the method is for preparing 4,4'-methylene diphenyl diisocyanate from a crude MDI mixture including, among others, different isomers of methylene diphenyl diisocyanate, namely 4,4'-methylene diphenyl diisocyanate and at least one of 2,2'-methylene diphenyl diisocyanate, 2,4'-methylene diphenyl diisocyanate, and MDI dimers, MDI oligomers, MDI polymers and lights.

In addition, it is preferred in an embodiment that the condensate is subcooled in the overhead vapor condenser to 47° C., preferably to less than 45° C., more preferably to at most 43° C. and most preferably to at most 42° C. The nearer the cooling temperature comes to 42° C., the more reliably the formation of dimers in the overhead vapor condenser loop is reduced as much as possible and in particularly a condensed liquid with a dimer content of less than 200 ppm is obtained.

In a further development of the idea of the present disclosure, it is suggested that the pressure at the top of the distillation column is set to 2 to 10 mbar and preferably to at most 3 mbar. This reliably allows to keep the bottom temperature of the distillation column well below 210° C., which contributes to a minimization of the formation of dimer.

In order to further reduce the dimer content in the condensed liquid, it is proposed in an embodiment to set the average residence time of the liquid in the tubes of the overhead vapor condenser (which is subsequently also called "overhead vapor condenser loop") to 30 seconds to 5 min and preferably to less than 1 min. The lower the average residence time of the liquid in the overhead vapor condenser loop, the lower the tendency for the formation of dimer.

All in all, it is particularly preferred in accordance with various embodiments of the present disclosure to perform the process so, i.e. to operate the plant so, that the condensed liquid withdrawn from the overhead vapor condenser has a dimer content of less than 200 ppm, preferably of at most 150 ppm, more preferably of at most 100 ppm, still more preferably of at most 70 ppm and most preferably of at most 60 ppm.

Preferably, in an embodiment, the ratio of reflux to condensate is set to 0.05 to 0.25, preferably to 0.10 to 0.20 and most preferably to about 0.15. A different ratio of reflux to condensate leads in tendency to a more efficient washing out of dimer from the ascending vapor by the descending liquid in the distillation column and thus to a decrement of the dimer content.

In accordance with another embodiment of the present disclosure, the condensed liquid withdrawn from the overhead vapor condenser is subsequently, i.e. downstream of the distillation column, fed as liquid feed into a dynamic crystallization apparatus, preferably a falling-film crystallization apparatus and more preferably a suspension crystallization apparatus.

As set out above, the condensed head product of the distillation column, i.e. the liquid feed into the dynamic crystallization apparatus, is preferably in an embodiment an isomeric monomer with a low MDI dimer content having the following characteristics:
i) a dimer content of less than 200 ppm, preferably of at most 150 ppm, more preferably of at most 100 ppm, still more preferably of at most 70 ppm and most preferably of at most 60 ppm, and/or
ii) a content of polymeric methylene diphenyl diisocyanate of at most 2000 ppm, preferably of at most 1500 ppm, more preferably of at most 1000 ppm and most preferably of at most 800 ppm, and/or
iii) a color of at most 100 APHA, preferably a color of at most 50 APHA, more preferably a color of at most 40 APHA, and/or
iv) a hydrolyzable chloride content of 10 to 150 ppm, preferably of 30 to 90 ppm, more preferably of 50 to 80 ppm and most preferably of 65 to 75 ppm, and/or
v) a content of 4,4'-methylene diphenyl diisocyanate of 88 to 96% by weight, preferably of 90 to 95% by weight and more preferably of 92 to 94% by weight.

Preferably, in an embodiment, the liquid feed into the dynamic crystallization apparatus fulfils at least two, more preferably at least three, even more preferably at least four at most preferably all of the aforementioned criteria i) to v).

Moreover, in an embodiment, it is preferred that the refluxed liquid is heated in the flow-controlled reflux system—in particular between downstream of the overhead vapor condenser and the distributor being arranged above the structured packing—to a temperature of 150 to 190° C., preferably to a temperature of 150 to 180° C. and more preferably to a temperature of about 180° C. Thereby, a fouling in the distributor can be reliably avoided.

During the crystallization in the suspension crystallization apparatus, the liquid feed is cooled at the surface of a crystallization zone to a temperature below the equilibrium freezing temperature of the liquid so that a crystal layer enriched in the isomeric monomer to be separated and purified is deposited on the surface, whereby a mother liquid having a lower concentration of the isomeric monomer to be separated and purified than the liquid feed is formed, wherein the liquid feed comprises 88 to 96% by weight, preferably 90 to 95% by weight and more preferably 92 to 94% by weight of 4,4'-methylene diphenyl diisocyanate.

The crystals formed during the crystallization are separated from the mother liquor preferably in a wash column apparatus so as to obtain the separated and purified isomeric monomer.

In accordance with a third aspect, an embodiment of the present disclosure relates to purified methylene diphenyl diisocyanate composition obtained as condensed head product of the distillation column, i.e. as condensate or condensed phase, respectively, after the distillation column, which has the following characteristics:
i) a dimer content of less than 200 ppm, preferably of at most 150 ppm, more preferably of at most 100 ppm, still more preferably of at most 70 ppm and most preferably of at most 60 ppm,
ii) a content of polymeric methylene diphenyl diisocyanate of at most 2000 ppm, preferably of at most 1500 ppm, more preferably of at most 1000 ppm and most preferably of at most 800 ppm,
iii) a color of at most 100 APHA, preferably a color of at most 50 APHA, more preferably a color of at most 40 APHA,
iv) a hydrolyzable chloride content of 10 to 150 ppm, preferably of 30 to 90 ppm, more preferably of 50 to 80 ppm and most preferably of 65 to 75 ppm and
v) a content of 4,4'-methylene diphenyl diisocyanate of 88 to 96% by weight, preferably of 90 to 95% by weight and more preferably of 92 to 94% by weight.

In accordance with a fourth aspect, an embodiment of the present disclosure relates to purified 4,4'-methylene diphenyl diisocyanate obtainable with the process including the crystallization stage described above, wherein the purified 4,4'-methylene diphenyl diisocyanate has at least one of the subsequent characteristics and preferably all of the subsequent characteristics:
i) a color of at most 100 APHA, preferably a color of at most 50 APHA, more preferably a color of at most 30 APHA and most preferably a color of at most 20 APHA,
ii) a hydrolyzable chloride content of at most 100 ppm, preferably of at most 50 ppm, more preferably of at most 30 ppm and most preferably of at most 15 ppm, and
iii) a content of 4,4'-methylene diphenyl diisocyanate of more than 98.4% by weight, preferably of at least 98.5% by weight and more preferably of more than 98.6% by weight.

Preferably, in an embodiment, the purified 4,4'-methylene diphenyl diisocyanate in accordance with the present disclosure fulfils at least two and more preferably all three of the above characteristics i) to iii).

BRIEF DESCRIPTION OF THE DRAWINGS

The invention will be explained in more detail hereinafter with reference to the drawings.

Figure 1:
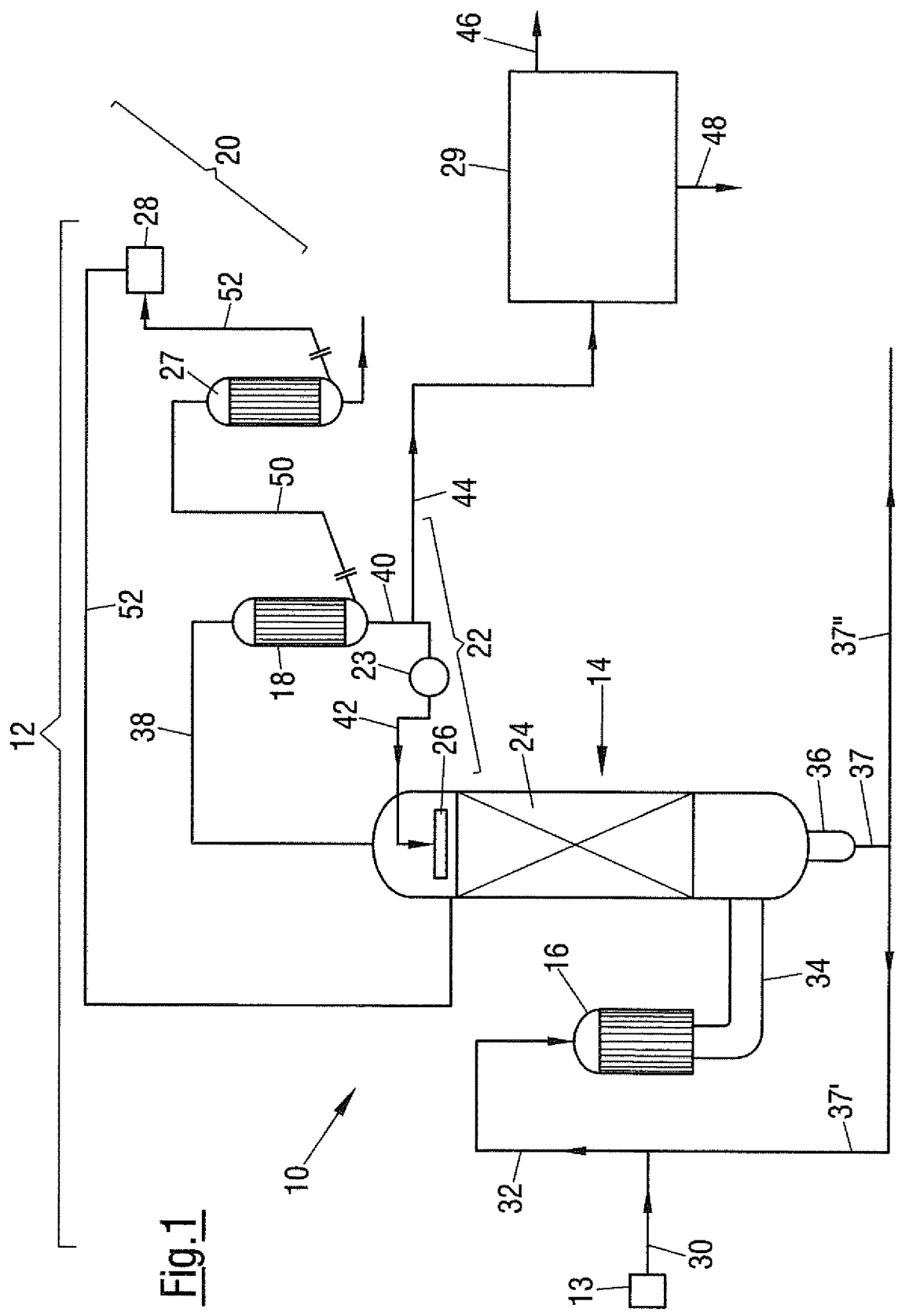
FIG. 1 schematically shows a plant for preparing purified 4,4' MDI from a crude MDI mixture according to an embodiment of the present disclosure, FIG. 2 schematically shows the suspension crystallization apparatus included in the plant shown in FIG. 1 and FIG. 3 schematically shows the wash column apparatus of the suspension crystallization apparatus shown in FIG. 2.

The plant 10 shown in FIG. 1 comprises a distillation apparatus 12, which comprises a source 13 for a crude MDI mixture, a distillation column 14, an evaporator 16, an overhead vapor condenser 18, an overhead vacuum system 20 and a flow-controlled reflux system 22. The flow-controlled reflux system 22 comprises a heater 23 and the distillation column 14 comprises a structured packing 24, above which an open channel splash distributor 26 is arranged. Moreover, a cold trap 27 is comprised between the overhead vapor condenser 18 and the overhead vacuum system 20 and a vacuum source 28 is comprised in the overhead vacuum system 20. In addition, the plant 10 comprises downstream of the distillation apparatus 12 a suspension crystallization apparatus 29.

The source 13 for a mixture of different isomeric monomers is connected via feed line 30 and line 32 with the evaporator 16, which is embodied as falling film evaporator. Via line 34, the falling film evaporator 16 is connected with the lower part of the distillation column 14. The distillation column 14 comprises a sump 36, which has a smaller diameter than the section of the distillation column 14 above the sump 36. The sump 36 is connected with a line 37, which splits into lines 37' and 37". While the line 37' is connected with the line 32 leading into the evaporator 16, the line 37" is an outlet line.

From the head of the distillation column 14, a line 38 leads into the overhead vapor condenser 18, which is embodied as shell and tube evaporator. The lower end of the overhead vapor condenser 18 is connected with a withdrawal line 40, which splits into a reflux line 42 and a line 44. While the reflux line 42 is connected with the heater 23 of the reflux system 22 and downstream thereof with the open channel splash distributor 26, the line 44 leads into the suspension crystallization apparatus 29. The suspension crystallization apparatus 29 has two outlet lines 46, 48.

The lower end of the overhead vapor condenser 18 is further connected with a vapor line 50, through which remaining vapor is withdrawn from the overhead vapor condenser 18. The vapor line 50 leads into the cold trap 27, from which a vacuum line 52 is connected with the vacuum source 28, from which the line 52 returns into the upper end of the distillation column 14.

During the operation, a crude MDI mixture including different isomeric MDI monomers, such as 2,2'-MDI, 2,4'-MDI and 4,4'-MDI, is fed from the source 13 via lines 30, 32 into the evaporator 16, where the liquid is evaporated. The generated vapor flows via line 34 into the lower part of the distillation column 14, where it ascends through the structured packing 24. In the structured packing 24, the ascending vapor is in intimate contact with descending liquid and the descending liquid washes a major part of the dimer formed in the evaporator 16 and the lower part of the distillation column 14 out of the ascending vapor. The vapor is withdrawn from the head of the distillation column 14 via the line 38 and transported into the overhead vapor condenser 18, where the vapor is liquefied and the condensate is directly subcooled to about 42° C. Moreover, the flow velocity of the vapor and the piping between the head of the distillation column 14 and the overhead vapor condenser 18 are adjusted so that the average residence time of the vapor within the overhead vapor condenser 18 is about 30 seconds to 5 minutes and preferably less than 1 minute. Due to the direct subcooling of the condensed liquid and the short residence time of the vapor in the piping, only traces of dimer are formed in the piping. Consequently, the condensed liquid withdrawn from the overhead vapor condenser 18 has a dimer content of less than 100 ppm, namely of about 60 ppm, and a concentration of 4,4'-MDI of about 92.5% by weight. A part of this condensed liquid is fed via line 44 into the suspension crystallization apparatus 29 for further purification, whereas the remaining part of the condensed liquid is returned via the flow-controlled reflux system 22 to the open channel splash distributor 26 of the distillation column 14. This reflux descends as liquid or washing fluid, respectively, down through the structured packing 24. A fraction rich in polymeric MDI is withdrawn from the distillation column 14 via line 37, from which a partial stream is returned via lines 37', 32 and 34 into the distillation column together with feed, whereas the remaining part of the fraction is withdrawn from the plant 10 via line 37".

The condensed liquid is further purified in the suspension crystallization apparatus 29 and leaves the plant via the outlet line 46, whereas the mother liquid of the crystallizer is withdrawn via the residue outlet line 48. The purified product leaving the plant via the product outlet line 46 has a content of 4,4'-MDI of at least 98.5% by weight.

Figure 2:
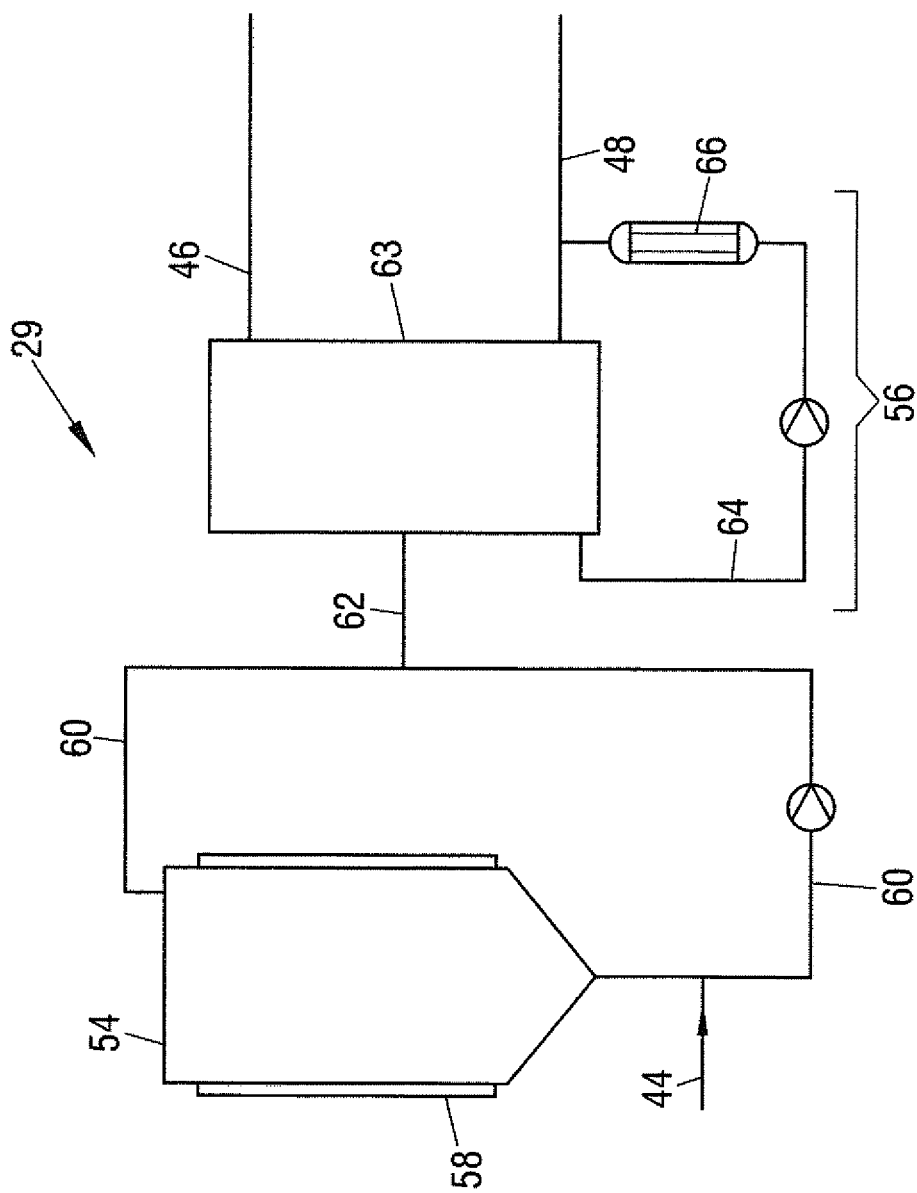

As shown in FIG. 2, the suspension crystallization apparatus 29 comprises a suspension crystallizer 54 and a wash column apparatus 56. The suspension crystallizer 54 is provided with a cooling system 58, which allows to cool the suspension crystallizer 54. The condensed liquid obtained in the overhead vapor condenser 18 is fed via line 44 into the circulation line 60, which connects the outlet at the lower end of the suspension crystallizer 54 and the upper end of the suspension crystallizer 54. A transfer line 62 leads from the circulation line 60 into the wash column apparatus 56. The wash column apparatus 56 comprises a cylindrical vessel 63, which is provided at its lower end with a circulation line 64, which in turn comprises a heater 66.

During the operation, condensed liquid obtained in the overhead vapor condenser 18 is fed via line 44 into the circulation line 60 and from this line into the upper end of the suspension crystallizer 54. The suspension crystallizer 54 is cooled via the cooling system 58 so that the mixture contained therein has a temperature of below the equilibrium freezing temperature of the liquid. On account thereof, crystals of pure or at least essentially pure 4,4' MDI are formed in the suspension crystallizer 54, whereas the 2,2' MDI and 2,4' MDI remains essentially in the mother liquid. A part of the suspension of crystals suspended in mother liquor is continuously discharged from the suspension crystallizer 54 via line 60, into which the feed is introduced via line 44. A part of the so formed mixture is returned into suspension crystallizer 54 via line 60, whereas the remaining part of this stream is transferred via transfer line 62 into the wash column apparatus 56. Alternatively to the embodiment shown in FIGS. 2 and 3, the transfer line 62 may be a line, which ends within the piston rod and opens out at the end of the piston rod ending in the piston head. In the cylindrical vessel 63 of the wash column apparatus 56, the crystals are separated from the suspension so as to obtain a crystal fraction and a mother liquor fraction. While the mother liquor fraction is withdrawn from the wash column apparatus 56 via the residue outlet line 46, the crystal fraction is withdrawn from the cylindrical vessel 63 of the wash column apparatus 56 into the circulation line 64 and guided through the heater 66, where the crystal fraction is heated so as to assure that all of the crystals are molten. A part of the crystal fraction is recirculated into the cylindrical vessel 63, whereas the remaining part of the crystal fraction is withdrawn from the wash column apparatus 56 via the product outlet line 48.

Figure 3:
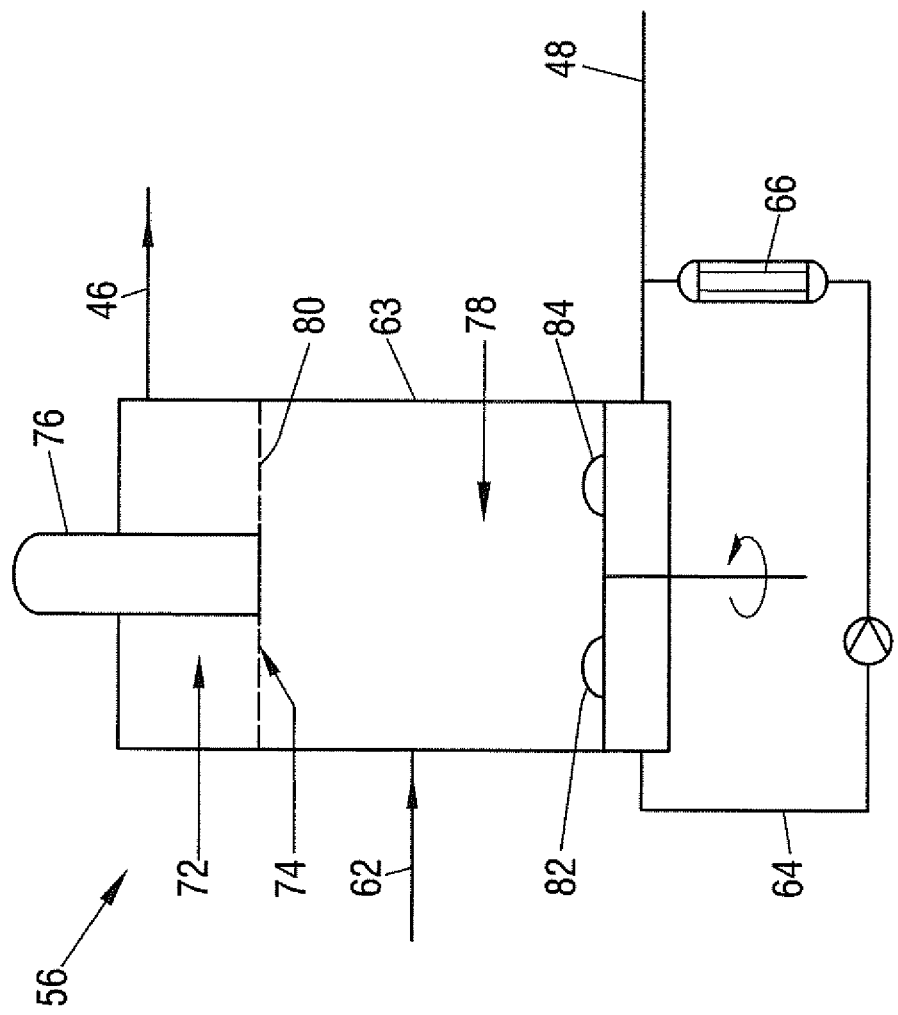

The wash column apparatus 56 of the suspension crystallization apparatus 29 is shown in more detail in FIG. 3. The wash column apparatus 56 comprises a cylindrical vessel 63, in which a piston 72 is arranged so as to be reciprocatingly movable in the cylindrical vessel 63. The piston 72 comprises a piston head 74 and a piston rod 76, wherein the piston 72 bounds above the piston head 74 a wash chamber 78 inside the cylindrical vessel 63. The piston head 74 comprises a filter means 80, which allows that mother liquor flows through the piston head 74, when the piston 72 is moved downwardly, while the crystals cannot flow through the piston head 74. The mother liquor passes the filter means 80 of the piston head 74 and is discharged from the cylindrical vessel 63 via the residue outlet line 46.

In the lower part of the cylindrical vessel 63 a scraper 82 is provided, which comprises two rotating discs 84.

The circulation line 64 is arranged in the lower part of the cylindrical vessel 63 below the scraper 82. The circulation line 64 comprises the heater 66.

In operation, the suspension including the crystals suspended in the mother liquor is fed via the transfer line 62 into the wash chamber 78 of the cylindrical vessel 63 of the wash column apparatus 29, where the crystals are separated from the mother liquor and washed. In the cylindrical vessel 63, the piston 72 is moved up and down in a controlled manner. When the piston 72 makes a suction stroke, i.e. when the piston is moved upwardly, a particular amount of suspension is introduced from the transfer line 62 into the wash chamber 78. When the predetermined amount of suspension is introduced into the wash chamber 78, the piston 72 is controlled to make a compression stroke, i.e. to move downwardly, which leads to a compression or compaction, respectively, of the suspension, since the suspension mixture is moved towards the scraper 82, in which a high resistance against further the vertical movement is subjected to the suspension. Therefore, a compacted crystal bed is formed in the lower part of the wash chamber 78. During the compression stroke of the piston 72, most of the mother liquor contained in the crystal suspension mixture is pressed through the filter means 80 of the piston head 74 and leaves the cylindrical vessel 63 via the residue outlet line 46.

The lowermost part of the crystal bed formed close to the upper end of the scraper 82 is comminuted by the scraper 82 and pressed by the pressure generated through the downwardly moved piston 72 into the circulation line 64, where it is pumped by means of a pump and heated via the heater 66 so as to melt the crystals to generate a crystal melt. A part of the crystal melt is removed from the plant via the product outlet 48, wherein the remainder of the circulated crystal melt is reintroduced into the cylindrical vessel 63 via the outlet of the circulation line 64. The crystal melt or wash liquid, respectively, flows upwardly through the crystal bed and displaces the mother liquor that is present between the crystals of the crystal bed and thus serves to wash out the crystal bed. Thus, the crystal melt in fact acts as wash liquid. During moving upwardly the crystal bed and displacing the mother liquor a wash front is formed at the phase boundary between the crystal melt and the mother liquor.

All in all, the wash column apparatus 29 leads to an efficient separation of mother liquor and crystals and also allows to obtain very pure 4,4' MDI crystals on account of an efficient washing of the crystals from the mother liquor before discharging the molten crystals as product from the plant 10.

The invention claimed is:

1. A plant for preparing a purified isomeric monomer from a mixture of different isomeric methylene diphenyl diisocyanate monomers, wherein the plant comprises a distillation apparatus, which comprises:
   a) a distillation column including a structured packing,
   b) a source for a mixture of different isomeric methylene diphenyl diisocyanate monomers,
   c) an evaporator,
   d) an overhead vapor condenser,
   e) an overhead vacuum system and
   f) a flow-controlled reflux system,
   wherein the source is connected with the evaporator, the evaporator is connected with a lower part of the distillation column via a line, the distillation column leads to the evaporator via another line, and a head of the distillation column leads into the overhead vapor condenser,
   wherein the overhead vapor condenser is connected to the flow-controlled reflux system and comprises a shell and tube arrangement configured to directly subcool condensate to less than 47° C., and the overhead vapor condenser is provided with a vapor outlet line, which is in fluid connection with the overhead vacuum system, which in turn is provided via a line in fluid connection with an inlet at an upper part of the distillation column, and
   wherein the flow-controlled reflux system comprises a heater configured to reheat a partial stream of the condensate formed in the overhead vapor condenser up to 190° C.

2. The plant in accordance with claim 1, wherein the plant does not comprise any further distillation column.

3. The plant in accordance with claim 1, wherein the plant further comprises, downstream of the distillation apparatus, a falling-film crystallization apparatus or a suspension crystallization apparatus, wherein the overhead vapor condenser is provided with a withdrawal line, wherein the falling-film crystallization apparatus or suspension crystallization apparatus is connected with the withdrawal line.

4. The plant in accordance with claim 1, wherein the source for the mixture of different isomeric monomers comprises different isomers of methylene diphenyl diisocyanate, which comprise 4,4'-methylene diphenyl diisocyanate and at least one of 2,2'-methylene diphenyl diisocyanate, 2,4'-methylene diphenyl diisocyanate, as well as dimers, oligomers and polymers thereof.

5. The plant in accordance with claim 1, wherein the overhead vapor condenser is configured to directly subcool the condensate to less than 46° C.

6. The plant in accordance with claim 1, wherein the evaporator is a falling film evaporator or a thin film evaporator.

7. A process for preparing a purified methylene diphenyl diisocyanate from a crude mixture including different isomeric methylene diphenyl diisocyanate monomers as well as dimers, oligomers and polymers thereof, wherein the process is performed in a plant in accordance with claim 1, wherein
   (i) the mixture of different isomeric methylene diphenyl diisocyanate monomers is fed from the source into the evaporator, where liquid is evaporated;
   (ii) generated vapor flows into the lower part of the distillation column; and
   (iii) vapor is withdrawn from the head of the distillation column and transported into the overhead vapor condenser, in which the condensate is directly subcooled to less than 47° C., wherein remaining vapor is withdrawn from the overhead vapor condenser, led through the overhead vacuum system and returned into the upper part of the distillation column, a portion of the condensate is returned via the flow-controlled reflux system into the distillation column and another portion of the condensate is withdrawn as purified isomeric monomer.

8. The process in accordance with claim 7, wherein the process is for preparing 4,4'-methylene diphenyl diisocyanate from a crude methylene diphenyl diisocyanate mixture including different isomers, dimers, oligomers and polymers of methylene diphenyl diisocyanate, wherein the mixture contains 4,4'-methylene diphenyl diisocyanate and at least one of 2,2'-methylene diphenyl diisocyanate, 2,4'-methylene diphenyl diisocyanate and oligomers thereof.

9. The process in accordance with claim 7, wherein the pressure at the top of the distillation column is set to 2 to 10 mbar.

10. The process in accordance with claim 7, wherein an average residence time of liquid in tubes of the overhead vapor condenser is adjusted to 30 seconds to 5 min.

11. The process in accordance with claim 7, wherein the process is performed so that condensed liquid withdrawn from the overhead vapor condenser has a dimer content of less than 200 ppm.

12. The process in accordance with claim 7, wherein the condensate withdrawn from the overhead vapor condenser has the following characteristics:
   i) a dimer content of less than 200 ppm,
   ii) a content of polymeric methylene diphenyl diisocyanate of at most 2000 ppm,
   iii) a color of at most 100 APHA,
   iv) a hydrolyzable chloride content of 10 to 150 ppm, and
   v) a content of 4,4'-methylene diphenyl diisocyanate of 88 to 96% by weight,
   wherein all of the criteria i) to v) are fulfilled.

13. The process in accordance with claim 7, wherein condensed liquid withdrawn from the overhead vapor condenser is subsequently fed as liquid feed into a falling-film crystallization apparatus or a suspension crystallization apparatus.

* * * * *